United States Patent [19]

Maurer et al.

[11] Patent Number: 5,500,970
[45] Date of Patent: Mar. 26, 1996

[54] AUTOMATIC TOOTHBRUSH

[75] Inventors: Wilhelm Maurer, Talacherring 15, CH-8103 Unterengstringen; Andreas Maurer, Zurich, both of Switzerland

[73] Assignee: Wilhelm Maurer, Switzerland

[21] Appl. No.: 162,144

[22] PCT Filed: Apr. 15, 1993

[86] PCT No.: PCT/CH93/00096

§ 371 Date: Dec. 14, 1993

§ 102(e) Date: Dec. 14, 1993

[87] PCT Pub. No.: WO93/20777

PCT Pub. Date: Oct. 28, 1993

[30] Foreign Application Priority Data

Apr. 15, 1992 [CH] Switzerland ............... 1261/92

[51] Int. Cl.⁶ ............ A61C 17/34; A46B 13/02
[52] U.S. Cl. .................... 15/22.1; 15/22.4
[58] Field of Search ............... 15/22.1, 22.2, 15/22.4

[56] References Cited

U.S. PATENT DOCUMENTS

| 3,570,035 | 3/1971 | Barnett | 15/22.1 |
| 3,588,936 | 6/1971 | Duve | 15/22.1 |
| 4,787,847 | 11/1988 | Martin et al. | 15/22.1 |
| 4,795,347 | 1/1989 | Maurer et al. | 15/22.1 |

FOREIGN PATENT DOCUMENTS

| 2038335 | 2/1972 | Germany | 15/22.1 |
| 3529861 | 2/1987 | Germany | 15/22.1 |

Primary Examiner—Edward L. Roberts, Jr.
Attorney, Agent, or Firm—Breiner & Breiner

[57] ABSTRACT

An automatic toothbrush to optimally clean at least two sides of a tooth or a row of teeth comprising a cleaning head with a substantially U-shaped support to which are mounted clusters of bristles. The clusters of bristles are mounted on self-positioning pivoting levers of the U-shaped support in order to clean even little accessible tooth locations. Using at least one mechanical and/or electromagnetic drive means, control is made possible of a phase-shifted, impulsive motion of the support relative to the automatic toothbrush and of the pivoting levers with the cleaning bristles relative to the support to implement a cleaning or wiping action by the clusters of bristles from the gum to the tooth crown while, in the opposite direction, the motion takes place with at least reduced pressure applied to the teeth.

19 Claims, 5 Drawing Sheets

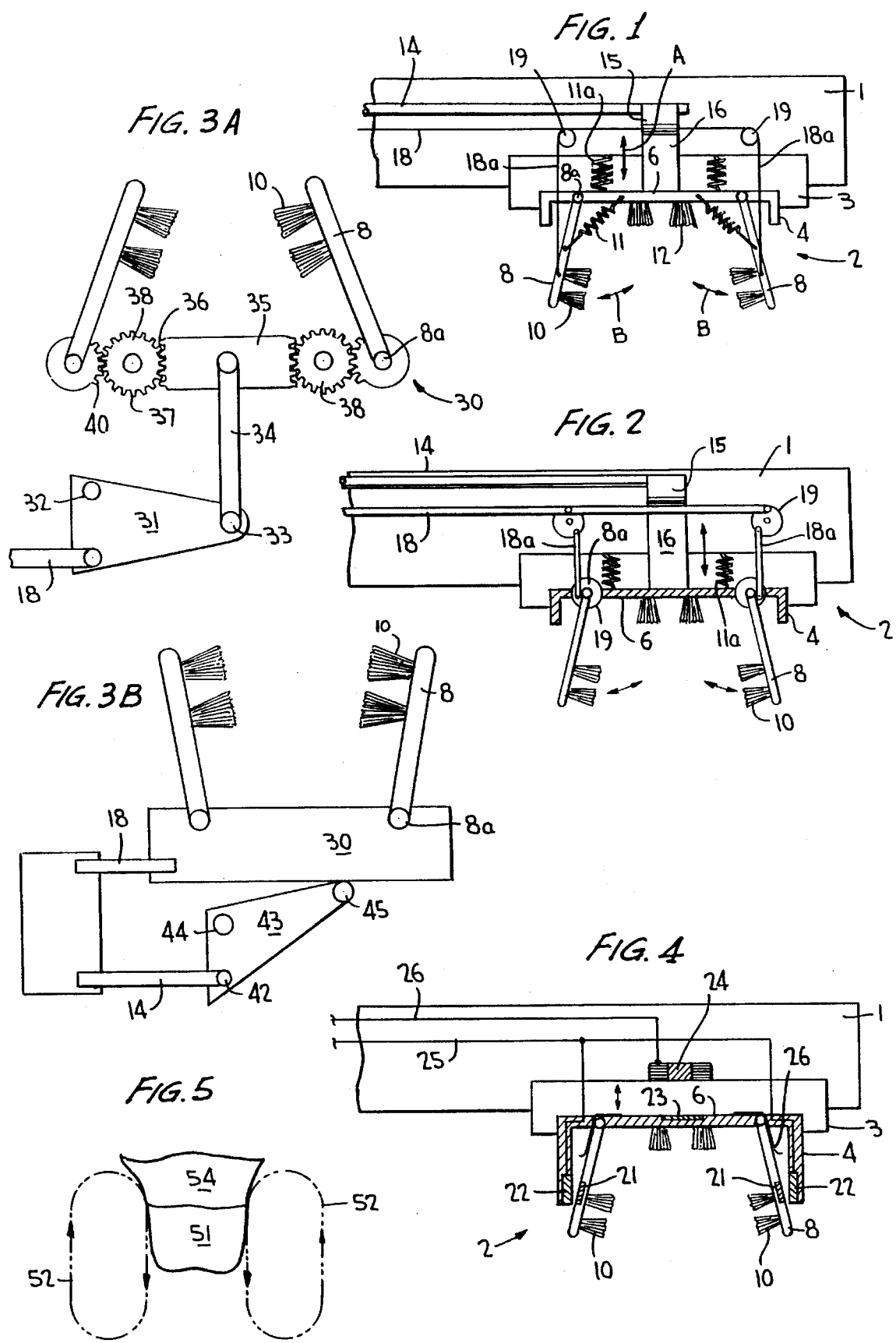

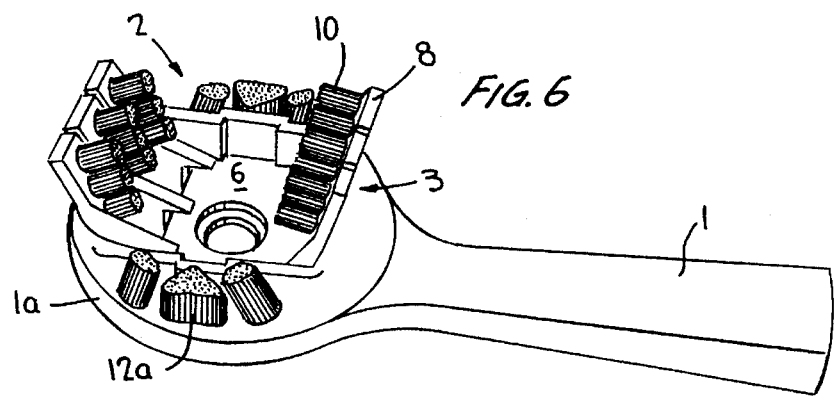
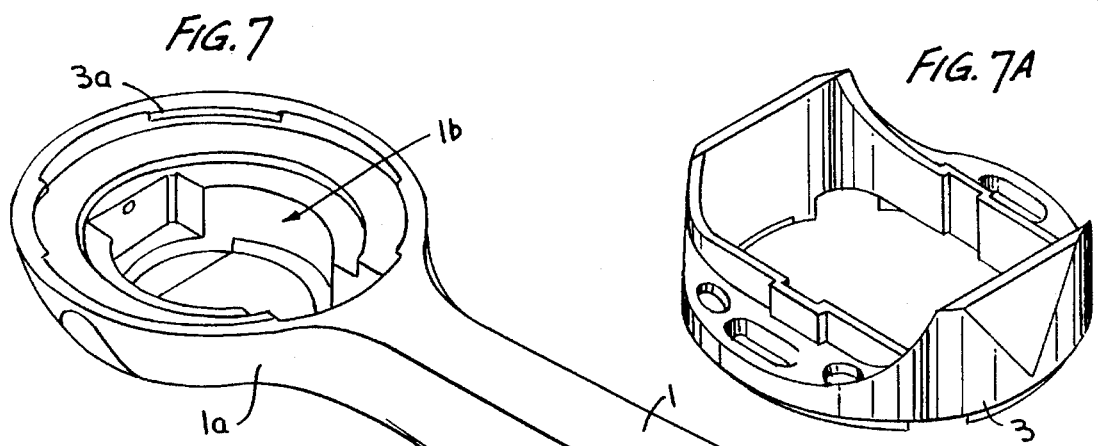
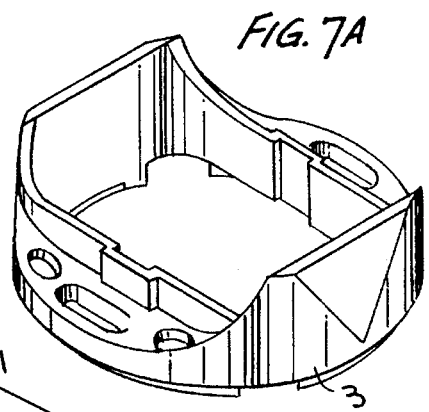
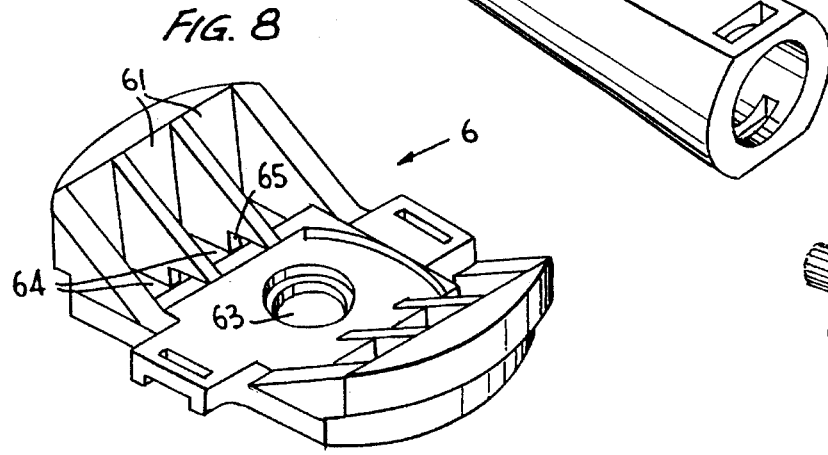
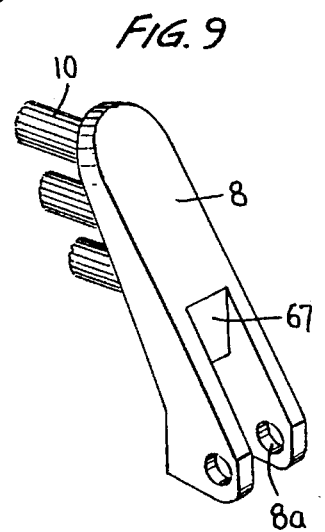
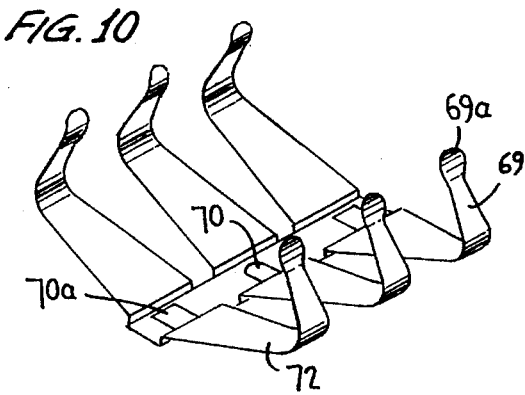

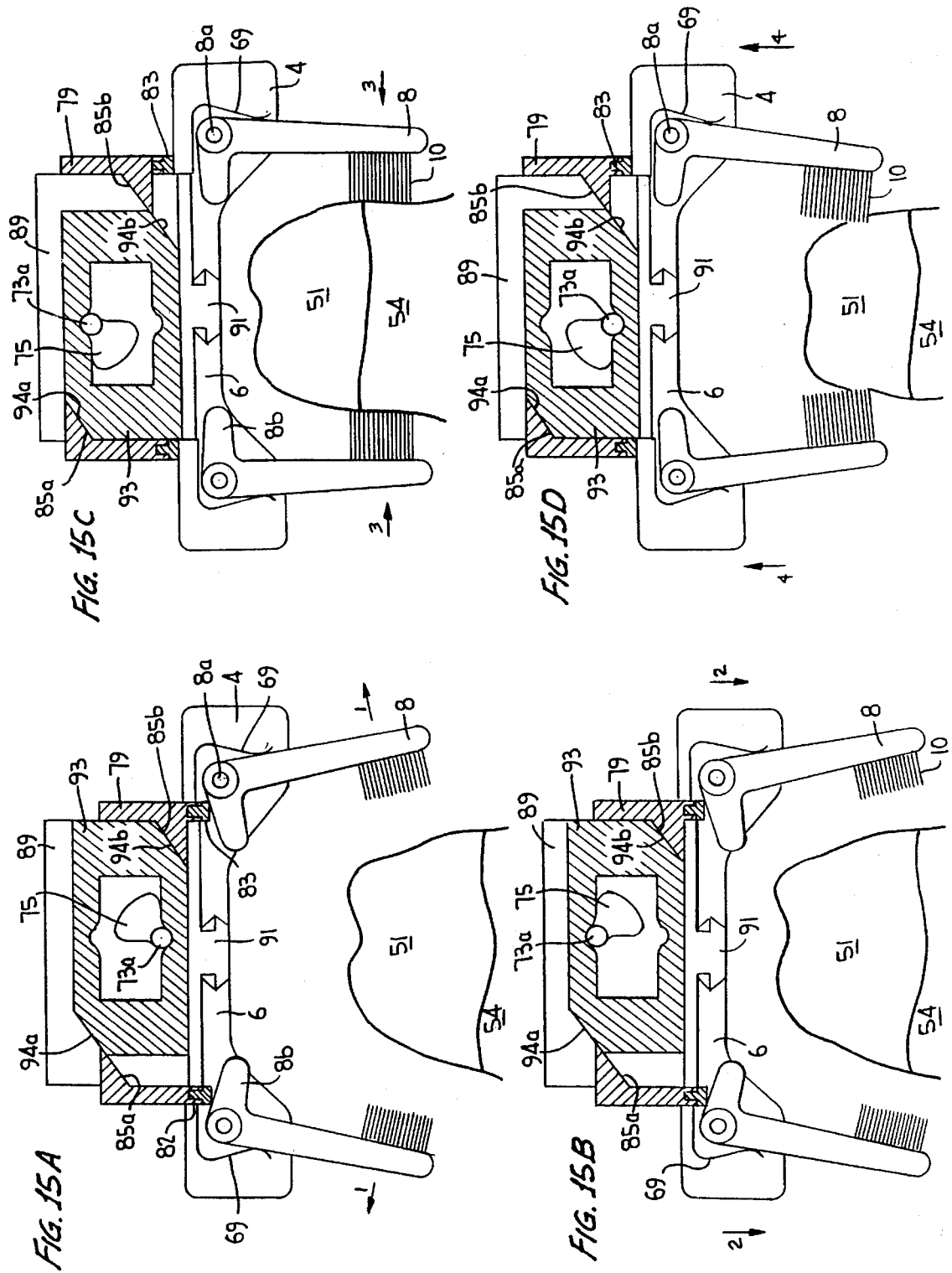

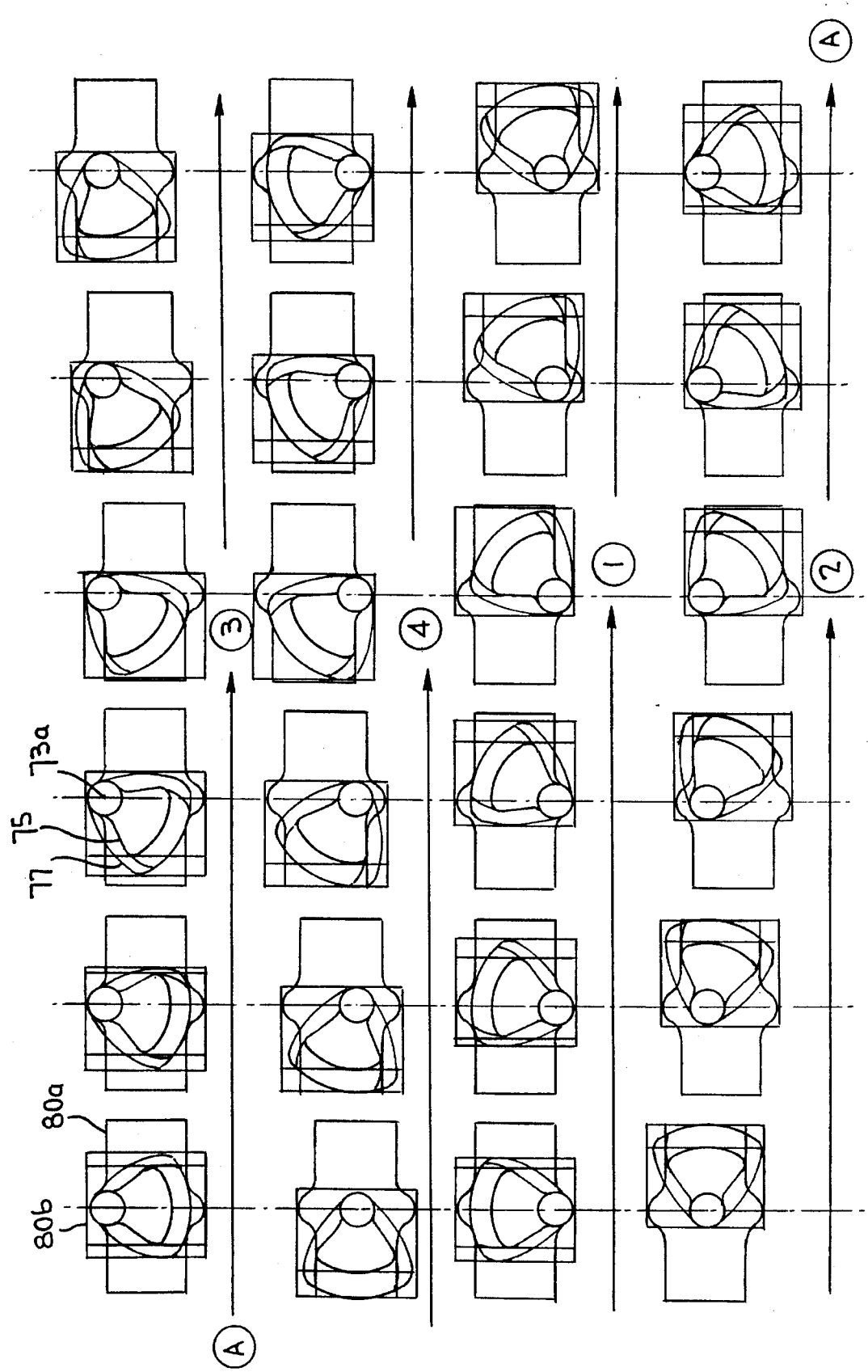

AUTOMATIC TOOTHBRUSH

The present invention concerns an automatic toothbrush having a drive means which enhances tooth cleaning using cleaning elements powered by the drive means.

The present invention is a further development of the dental cleaning system of the European Patent Application No. 0,173,114 such that the present patent application represents a continuation and completion of the European patent application.

As described in the European patent application, it is essential that the various dental surfaces be cleaned equally well when using a cleaning device. It is also critical to clean uniformly well to the extent possible the inner dental surface, i.e., that surface facing the oral cavity, as well as the gums and the outer dental surface, i.e., that surface facing the cheek. Again, it is important to assure an optimal local cleaning pressure on all sites to be cleaned. Lastly, the cleaning elements are to carry out optimal motions, namely, from the gums to the dental crown in as axially a direction as possible along the tooth while barely in the opposite direction.

The description of the above-European Patent Application No. 0,173,114 which is referred ti U.S. Pat. No. 4795,347 and is referred to for the fundamentals and it is thereby made an integral component of the present application. The method for cleaning teeth using a toothbrush wherein it is important that the cleaning be simultaneously carried out on at least two sides of the teeth as defined in the European patent application is especially significant in the present patent application. The defined methods of the invention disclosed in European Patent Application No. 0,173,114, as well as the equipment features of the defined automatic toothbrush, when combined with the subsequently defined features of the present invention are substantive characteristics of the present patent application.

As regards European Patent Document Application No. 0,173,114, the various motions of an automatic toothbrush of the invention are predominantly carried out using pneumatically or hydraulically powered drive members. Even though the hydraulically or pneumatically actuated drive members are in themselves practical, it is the object of the present invention to further refine and simplify the drive mechanism to achieve both a higher operational reliability of automatic toothbrushes while lowering the manufacturing costs and making possible more compact cleaning heads.

The problem of an automatic toothbrush are solved by the invention as defined herein.

The invention proposes a dental cleaning system, i.e., an automatic toothbrush with a drive means to enhance tooth cleaning using powered cleaning elements. The toothbrush comprises at least one mechanical and/or electromagnetic drive means operationally linked to the cleaning elements in order to power at least part of the cleaning elements and/or sections thereof for at least two sequences of motion.

An automatic toothbrush as defined in the invention preferably comprises a grip, illustratively, enclosing a drive motor or an electrical connector, and a main head which can be detachably plugged onto the grip. The cleaning elements are present at or in a cleaning head mounted at least substantially at the end of the main head. At least part of the cleaning elements are mounted in the cleaning head in such a way that at least two sequences of relative motion relative to the main head will be initiated. Preferably, the cleaning head is connected in at least a rotatable and/or pivotable manner with the main head.

The drive means powered by the drive motor is/are designed in such a manner in the regions of the main head and cleaning head that the effective linkage passes through the connection between the main head and the cleaning part in such a way that at least part of the cleaning elements undergo the two relative motions about the main head.

Preferably, the cleaning head is in two parts, one part being movably connected to the other.

The invention requires that the teeth shall be cleaned at least on two sides simultaneously by the cleaning elements. The cleaning head preferably comprises a support which is seen as concave when viewed from a tooth. The cleaning elements are mounted on at least two sides of the support, preferably, on the inside of the concave part in order to enclose the teeth. The concave support defined by the invention can form one of the two parts of the cleaning head. Preferably the support is U-shaped with cleaning elements mounted at least at the two legs and facing inward.

Preferably the support or the cleaning part is essentially resting at the main head while being jointly rotatable and/or pivotable with the other part. The support where called for also is mounted on the other part in a relatively displaceable manner.

The drive means of the invention is at least one mechanical and/or electromagnetic unit which produces at least two motions. At least some of the cleaning elements or sections thereof are mounted to the support.

The U-shaped support on the one hand comprises a base and, on the other hand, a leg segment which on each side rests terminally in a pin or in the vicinity of the base and are mounted in a mutually linearly displaceable manner along a reference direction pointing toward the legs.

On one hand, the drive means is/are operationally connected to the support base to carry out a stroke motion of the base relative to the main head or the other part of the cleaning head and, on the other hand, is/are operationally linked with the leg segments to carry out a pivoting excursion of the segments relative to the base and about the pins mounted in the vicinity of the base.

The drive means preferably is/are provided for one particular cyclic motion of the base and leg segments. The cleaning elements moving along, preferably, two-dimensional paths in the U plane of the support, with the path segments pointing toward the plane of symmetry of the U being crossed toward the support base, i.e., the main head.

Preferably, the leg segments rest on the support base while being pre-stressed toward the plane of symmetry of the U, whereby the motion of the cleaning elements at the leg segments and the cleaning pressure take place from the root toward the crown of a tooth and then back with at least reduced pressure while being powered by the drive means acting in the direction opposite the pre-stressing.

In a similar and further embodiment of the automatic toothbrush of the invention, the support of the cleaning head is so controlled using cyclic phase-shift relative to the leg segments that upon motion of the support, i.e., of the support base, in a direction substantially perpendicularly away from the main head, the leg segments assume their widest pivoted-apart positions and upon the opposite motion by the support, i.e., by the support base, the leg segments are arranged in mutually converging pivoted positions.

In one embodiment, at least one drive means in the form of a shaft is provided and this shaft comprises at least two mutually different excentric sections in the region of the connection. Each section implements a motion of at least some of the cleaning elements.

Preferably, the shaft rotates in a substantially uniform manner and one of the two excentric sections are operationally linked to the support, i.e., the support base carries out the excursion relative to the main head. The other shaft section is operationally linked to the leg segments to carry out the pivoting motions relative to the support base. The two sections are mutually so angularly offset at the shaft that the two motions of the support and leg-segments are carried out with a phase shift.

Preferred embodiments with cleaning elements driven by a shaft as above defined in an automatic toothbrush of the invention are defined in herein.

In lieu of the above defined drive shaft of the invention, the cleaning elements also can be powered by cables to carry out the minimum of two motions. Preferred embodiment variations of an automatic toothbrush of which the cleaning elements are powered by cables are described.

Instead of cables, one or more rocking camshafts also can be used to implement the two motions. Further, kinematic drives can be used. Also gears can be inserted between the drive means and the cleaning elements.

Further embodiments of the automatic toothbrush of the invention are also described.

Electromagnetic drive means furthermore can be used instead of mechanical ones, in which case ferromagnetic components can be mounted on one hand in the region of the cleaning elements to the cleaning head and, on the other hand, electromagnets at opposite segments of the cleaning head and/or at the main head, so that when these electromagnets are energized they shall implement the motions of the cleaning elements. Obviously, the arrangement can also be reversed. The ferromagnetic components can be affixed to the main head segments opposite the cleaning elements and the electromagnets in the region of the cleaning elements.

The ferromagnetic-fitted cleaning element can be mounted to be pre-stressed away from the oppositely arrayed electromagnets so that when the electromagnet is inactive, the cleaning elements are driven away from the electromagnets. However, the pre-stressing means does not need to be employed and the cleaning elements then will be freely displaceable, i.e., supported slackly when the electromagnets are inactive.

Obviously all the above drive means such as shafts, cam shafts, cables, kinematics, electromagnets, and the like can also be combined with one another.

As already mentioned above, it has been found advantageous to keep essentially constant the cleaning pressure applied by the cleaning elements to the teeth during the entire cleaning procedure. It is also advantageous to pre-stress the support leg segments using leaf-spring pre-stressing means acting on the opposite sides of the cleaning elements against the plane of symmetry of the U of the support. These leaf springs almost act from the back side on the leg segments and are mounted in such a way to the support base that during pivoting of the leg segments, the pivot point of the base shifts essentially in the longitudinal direction of the base in such a manner that, on account of uneven lever action, the spring force will be different and thereby the compression by the cleaning elements of the teeth to be cleaned remain approximately constant.

In another embodiment of the invention, an automatic toothbrush comprises a main head or a cleaning head, which is rotatable by about 180° about the grip to allow cleaning of the upper and lower teeth while holding the grip in the same manner.

The invention is elucidated in an illustrative manner in relation to the attached Figures in the description below.

FIG. 1 is a schematic longitudinal section of an embodiment of a cleaning head of an automatic toothbrush of the invention.

FIG. 2 is a longitudinal section of another embodiment of a cleaning head.

FIGS. 3a and 3b are schematic longitudinal sections of another embodiment of the drive means for the cleaning elements in a cleaning head.

FIG. 4 is a longitudinal section of another embodiment of a cleaning head of the invention.

Figure 11:
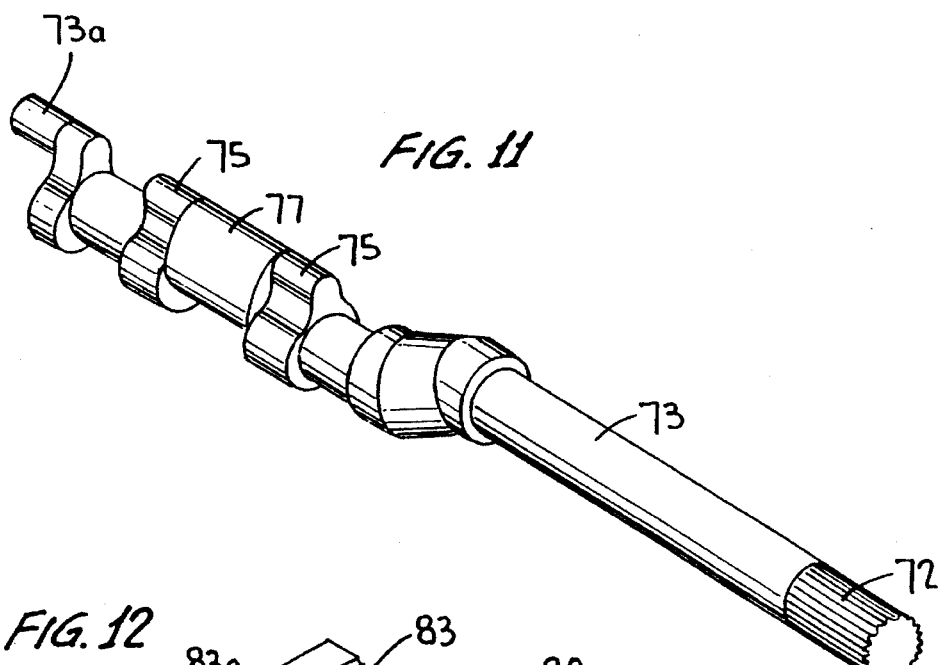

FIG. 5 schematically shows the motions of the cleaning element of one of the cleaning heads of FIGS. 1 through 4.

FIG. 6 is a schematic longitudinal perspective of another embodiment of a cleaning head of the invention.

FIGS. 7 through 14 show individual elements on an enlarged scale of the cleaning head of FIG. 6.

FIGS. 15a through 15d are schematic longitudinal sections of the cleaning head of FIG. 6 and of its operation.

FIG. 16 schematically shows the motion of the drive shaft in the cleaning head of FIG. 6 for a plurality of shaft positions as seen in the shaft longitudinal direction.

FIG. 1 is a longitudinal section of a cleaning head of the automatic toothbrush of the invention. The grip is omitted from the Figure. A cleaning head 2 is mounted to the end of the main head 1 to which the cleaning head is linked in a manner which allows it to rotate about its central axis. The cleaning head 2 consists of a pan-shaped component 3 and of a U-shaped support 4 composed of a base 6 and lateral leg segments 8 which are each pivotable about a pin 8a. The support 4 is mounted in a transversely displaceable manner to the main head 1, i.e., the support 4 is able to reciprocate transversely to the main head 1. Inside, clusters of cleaning bristles 10 are mounted on the leg segments, i.e., levers 8, and a cluster of cleaning bristles 12 can also be affixed to the support base 6.

In order to carry out its reciprocating motion, the support 4 is borne by a cylindrical unit 16 so as to be displaceable transversely to the main head 1 and is connected to a camshaft 14. A cam 15 is affixed to the camshaft to move the support 4 away from the camshaft 14. As soon as the cam 15 has been rotated to the side of the camshaft opposite the support 4, support 4 is retracted, for example, by springs 11a, toward the main head 1. The double arrow A schematically shows the reciprocating motion of the support 4 consisting of the base 6 and levers 8 with cleaning elements 10 and 12.

The to-and-fro pivoting motion of the levers 8 about the pins 8a, schematically-indicated by the double arrow B, is implemented in each case by a cable 18 connected by means of direction-changing rollers 19 and separate cable segments 18a to one of the levers 8. When the cable 18 is pulled, the two levers together with the cleaning bristles 10 are drawn away from the central axis of symmetry of the U-shaped support 4. Whereas, when the cable 18 is released, the two springs 11 pull the two levers back toward the axis of symmetry of the support 4.

Preferably, the two drive means 14 and 18 are synchronously gauged so that during the movement of the support 4 away from the main head, the two levers 8 dwell in the rearward pivoted open position whereas during the return motion of the support toward the main head 1, the two levers 8 are pivoted toward the center. FIG. 5 more comprehensively represents the motions of the cleaning bristles. The drive shaft 14 as well as the cable 18 can be powered by any arbitrary mechanism or assembly. Advantageously, there is a single drive unit, illustratively, the synchronous drive for the two components being a suitable drive divider.

FIG. 2 is a longitudinal section of a cleaning head basically the same as that of FIG. 1. However, the cable 18 is replaced by a bar kinematics linked by direction-changing rollers 19 and link rods 18a to the associated drive disks 8a of the two levers 8. Again, a camshaft 14 with a cam 15 is provided for the reciprocation of the support 4. FIG. 2 shows the cam 15 in a position away from the support 4, thus it is in its retracted position.

The advantage in using the link rod kinematics 18 is the difficulty in finding suitable plastics for cables meeting the requirements of such a complex arrangement. However, such requirements would be fully met when using high-grade plastics such as polyamide 12 or aromatic polyamides, such as aramide. It is important that such materials used for cables be practically stretch-free while being quite elastic and highly abrasion-proof. Moreover, there must be low water-absorption and chemical resistance in view of the cleaning substances ordinarily used in cleaning teeth.

Another advantage offered by a kinematics 18 is that return springs 11 can be eliminated since the to-and-fro motion of the levers 8 can be implemented by rocking the rotary disk 8a. This requirement, however, also can be met by using double cables, i.e., cables in the forward and backward directions.

FIGS. 3a and 3b are schematic longitudinal sections of another embodiment of the cleaning elements in the support 4. FIG. 3a shows the drive, i.e., the to-and-fro pivoting motion of the two levers 8. FIG. 3b shows the reciprocation of the support 4 relative to the main head 1.

In FIG. 3a, a rod-like component 18 again rocks a pivoting component 31 about a pin 32. A rod 34 rotatably connected by a pin 33 with the component 31 moves up and down a unit 35 fitted with a toothing 36 on each side. A gear 38 meshes on each side with the toothing 36. The toothing 37 meshes with the toothing 36. The toothing 39 at the opposite side at the toothing 38 meshes with a corresponding toothing 40 at the lever 8 to rock it about the pin 8a. If a pull is then exerted on the rod 18, then the rod 34 and the unit 35 also are pulled downward, as a result of which the geared transmission of this motion pivots the lever 8 from the axis of symmetry of the U toward the outside. By an opposite motion of the rod 18 toward the component 31, the rod 34 and the unit 35 are forced upward, whereby both levers are pivoted inward.

In FIG. 3b, the drive means of FIG. 3a are schematically indicated in the form of a black box and are denoted by the reference 30 which as a whole and together with the two levers 8 implements the vertical reciprocation. The reciprocation drive is implemented by providing a further rod 14 which again drives a component 43 rotatable about a pin 44 against the support and away from it. Preferably, a roller-like component 45 is present at the end of the component 43, as a result of which the black box 30 reciprocates as if resting on rollers. Again the synchronized control of the two drive rods 14 and 18 makes possible the motions described in relation to FIG. 1.

Again, FIG. 4 shows a longitudinal section of a main head 1 of an automatic toothbrush of the invention which comprises a terminal cleaning head 2 consisting of the pan 3 and the support base 4 carrying out the reciprocating vertical motion. The drive means for the vertical reciprocation of the support 4, i.e., of the support base 6 and further the drive means for the rocking motion of the two levers 8 with the cleaning bristles 10, is not implemented mechanically in FIG. 4, but rather electromagnetically. An electromagnet 24 for the vertical reciprocation of the support base 4 consists of a metal unit and coil fed from an electric line 26. A metal part, i.e., a matching pole piece 23, is mounted on the support base 6 opposite the electromagnet 24 and, upon energization of the electromagnet, can be attracted by it. The corresponding opposite motion away from the electromagnet 24 can be implemented either by reversing the electromagnet pole arrangement or by using springs analogous to those shown in FIG. 1.

The pivoting motions of the two levers 8 take place in a similar manner. Electromagnets 22 powered through a line 25 is mounted in the U-legs of the support 4. By mounting corresponding pole-pieces, i.e., metal elements 21, on the terminal sides of the two levers 8 opposite the cleaning bristles, the levers each can be attracted by the electromagnet 22 once it is energized. The inward pivoting motion of the two levers 8 preferably is implemented using leaf-spring components 26 mounted on the back sides of the two levers 8 and acting on them.

FIG. 5 schematically shows the preferred motions of the cleaning bristles 10 when cleaning and massaging the gums and teeth. The motions of the inward pointing cleaning bristles 10 mounted on the levers 8 is indicated by the two paths 52 covered on both sides, i.e., front and back sides of a schematically shown tooth. The cleaning bristles move away from the tooth toward the gum region 54 and thereupon the path is at its extreme from the region 54, next passing against the tooth 51 away from the gum region 54 toward the tip of the tooth 51. Once having passed the tip of the tooth 51, the levers 8 of FIGS. 1 through 4 pivot outward, reducing the bristle cleaning pressure at the tooth and then being moved again toward the gums 54.

FIG. 6 is a perspective of an illustrative preferred embodiment of a cleaning head 2 at a main head 1. A pan 3 is sat on the terminal region 1a of the main head and is connected to it in rotatable manner. The pan 3 comprises lateral cleaning bristles 12a to clean foremost the buccal tooth side. A planar base 6 is present centrally at the pan 3 and comprises sets of preferably three levers or leg segments 8 pivotably connected to it and evincing inwardly mounted cleaning bristles 10. The individual parts of the main head and cleaning head of the invention of FIG. 6 are discussed in detail and more comprehensively below in relation to FIGS. 7 through 14.

FIG. 7 shows a perspective of the main head 1 with a terminal part 1a comprising an inner and essentially circular recess 1b to receive and support the cleaning head. Channels 3a are present at the terminal edge zone of this recess 1b to rotatably receive the pan 3 which is shown in FIG. 7a without the corresponding cleaning bristles 12a.

FIG. 8 shows the support base 6 which comprises a central clearance 63 that is discussed further in relation to FIG. 15. The base 6 furthermore comprises on each side three clearances 61 to receive corresponding levers 8 as shown in FIG. 9. The levers 8 are retained in the clearances 61 by means of bolts (not shown) which extend through the corresponding pin orifices 8a in the levers 8 and through the clearances 65 in the base 6. As a result, the levers are supported on the base 6 while being pivotable about the axis 8a. Furthermore, the clearances 61 are open in their lower region, that is, apertures 64 are present below the levers 8. The significance of these apertures 64 is discussed more comprehensively in relation to FIGS. 15a through 15d.

On its, inside, the lever 8 shown in FIG. 9 comprises three clusters of cleaning bristles 10, although obviously a different bristle arrangement also can be chosen. At its opposite side, there is a rest surface 67 on lever 8 for the frictional rest of a corresponding, terminal contact section 69a of a spring system 69 as shown in FIG. 10. The spring system 69 of FIG. 10 is directly affixed to the support base 6 in such a manner that the individual spring segments pass underneath the levers 8 in order to compress by terminal sections 69a the back-side rest surface 67. The leaf-spring type arrangement 69 drives all six levers 8 toward the central plane of symmetry of the support. By means of clearances 70 and 70a, the pre-stressing spring system 69 can be made to snap into the base 6.

Figure 12:
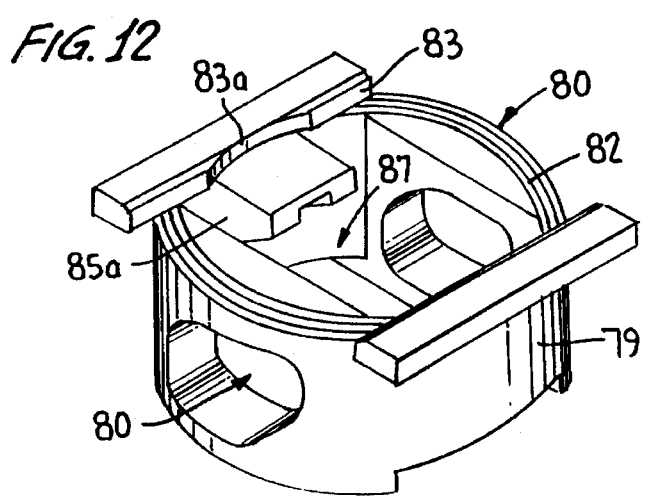

FIG. 11 shows the shaft 73 not visible in FIG. 6 used to implement the vertical reciprocation of the support, i.e., of the base 6, and also to implement the inward/outward pivoting motions of all six levers 8 with cleaning bristles 10. Illustratively, the drive shaft 73 itself can be powered-by a terminal toothed section 72 and the linkage passing through the main head 1 and grip. Preferably, the drive action is carried out in a linearly rotating manner about the axis 73a. As demanded by the invention, the drive shaft 73 comprises at least two differently excentric sections, of which the first includes the central zone 77 and the other the two identical adjoining side zones 75. The shaft 73 passes through apertures 80 in the sidewalls of an annular shell 79, shown in FIG. 12, with an inner cavity 87 which is perpendicular to the shaft and which is provided for mounting in the clearance 1b of the main head 1 of FIG. 7. At its top side, the shell 79 comprises a grooved annular termination 82 receiving in a freely rotatable manner two rest units 83 running on ball bearings in the terminal. Only one rest unit 83 is shown in FIG. 12 for ease of illustration. The other rest unit is positioned opposite the rest unit 83 shown in FIG. 12, as illustrated in FIGS. 15a–15d. The significance of these rest units 83 is discussed below in relation to FIGS. 15a through 15d.

Figure 14:
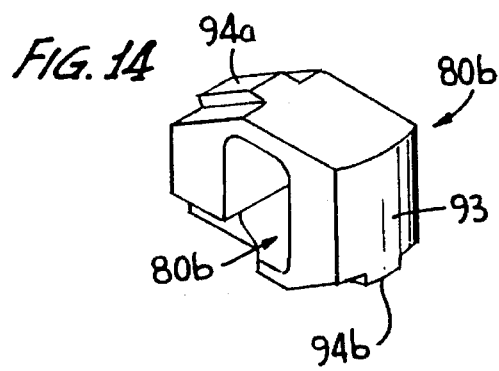
Figure 13:
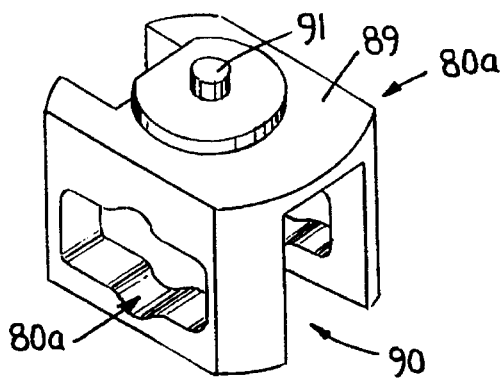

The shell 79 furthermore comprises a stop 85a pointing toward the cavity 87, the significance of which is discussed below in relation to FIG. 14. A base unit 89 shown in FIG. 13 is mounted in the cavity 87 and comprises apertures 80a of its own in the zone of the two apertures 80. The shaft 73 of FIG. 11 also passing through apertures 80a. The base unit 89 comprises a channel 90 present on its inside and running transversely to the shaft. A carriage 93 as shown in FIG. 14, is supported in a reciprocating manner in channel 90. At its topside, the base unit 89 comprises a pivot 91 upon which the support base 6 rests in rotatable manner. The pivot 91 passes through the central aperture 63 of the base. The carriage 93, shown in FIG. 14, furthermore comprises a corresponding aperture 80b both centrally and in the zone of the aperture 80a to also pass the shaft 73 of FIG. 11. The carriage 93 can be made to move in a reciprocating manner transversely to the shaft in the channel 90 of the basic unit 89. When moving in one direction, the sliding part 94a hits the stop 85a of the annular shell 79 and thereby forces the shell 79 upward. When the carriage 93 is moved in the other direction, then the corresponding sliding part 94b hits the stop 85b (not shown in FIG. 12) mounted on the annular shell 79 opposite the stop 85a. As a result, the shell 79 is forced downward. The just mentioned motions are discussed further below in relation to FIGS. 15a through 15d.

As already illustratively discussed above in relation to FIGS. 1 and 5, it is essential for the synchronized sequence of cleaning to adopt the design of the two clearances, i.e., apertures 80a and 80b of the basic unit 89 and carriage 93 respectively. By means of its two identical parts 75, the shaft 73 engages the two clearances or apertures 80a of the basic unit 89 whereby the basic unit 89 is reciprocated transversely to the direction of the shaft and vertically. In other words, the base unit 89 and thereby the support 6 is driven away from the main head and back toward it by means of the sections 75. The other section 77 engages the aperture 80b of the carriage 93 which thereby is moved transversely to the above mentioned reciprocation of the base unit 89 along the channel 90 until the carriage 93 by its corresponding part 94a hits the stop 85a of the shell, 79 which then, in a motion superposed to the reciprocation of the base unit 89, forces the shell upward.

The precise operation and the sequence of motions of the individual components discussed above in relation to FIGS. 8 through 14 are now elucidated in relation to FIGS. 15a through 15d.

FIG. 15a is a longitudinal section of the cleaning head of FIG. 6 (pan 3 being omitted) when ready for the movement of the support 4 in its phase away from the main head (not shown). On account of the position of the shaft sections 75 pointing in the direction away from the shaft axis 73a toward the main head, the base unit 89 and the carriage 93 are in their so-called retracted positions. The carriage 93 impacting by its sliding part 94b the corresponding stop 85b of the annular shell 79, this shell is in the position far from the main head 1. As a result,the rest unit 83 mounted by ball-bearings in the annular channel 82 passes through the clearances 64 of the base 6 to abut projections 8b of the two shown levers 8 which thereby are forced away from the plane of symmetry, i.e., from a schematically shown tooth 51, into an outward pivoted position.

Since the rest unit 83 is rotatably supported on the annular shell 79 and the support base 6 is rotatably mounted on the pivot 91, the support base 4 as a whole is rotatable relative to the main head. This is an important feature because it allows matching the cleaning bristles 10 to the particular tooth position during cleaning. As already mentioned, the pan 3 also is rotatably supported by the main head 1 whereby the entire cleaning head is rotatable relative to the main head and, thus, is able to match its position any time to that of the corresponding tooth.

On account of the outward pivoting motion of the levers 8 and hence of the cleaning bristles 10, the cleaning head of FIG. 15a is ready to be moved against the tooth 51 to be cleaned and the gums 54. This outward motion of the levers 8 is schematically shown on the side by the arrow 1.

Next the shaft 73 is rotated and, as shown by FIG. 15b, the shaft section 75 of the shaft axis 73a extends from the main head toward the tooth 51 to be cleaned. Thereby the base unit 89, the carriage 93 and the annular shell 79 are simultaneously forced against the tooth 51 to be cleaned. Both levers 8 remain in their outwardly pivoted position away from the tooth 51. The motion toward the tooth 51 as shown in FIG. 15b is indicated on the side by the arrow 2.

When the shaft 73 is rotated further in this direction, the section 77, not visible in FIGS. 15a through 15d, engages the aperture 80b of the carriage 93 which thereby is forced into the channel 90 toward the opposite side relative to the base unit 89, whereby the sliding part 94a of the carriage 93 hits the stop 85a of the annular shell 79 and retracts the shell 79 toward the main head. As a result, rest unit 83 also is retracted. Next, the leaf springs 69 resting pre-stressed against the back side of the levers 8 force the levers together with the cleaning bristles 10 against the tooth 51 to be cleaned, i.e., in the zone where gums 54 adjoin the teeth. The motion carried out in FIG. 15c is schematically indicated by the arrow 3 on the side.

Further rotating the shaft 73 in the same direction, section 75 again engages the aperture 80a in the base unit 89 to force it back against the main head. The carriage 93 and the annular shell are retracted at the same time. On account of this rearward motion, the support also is retracted and as a result the cleaning bristles 10 carry out their cleaning from the gum boundary 51a to the top of the tooth. The motion implemented in FIG. 15d is indicated on the side by the arrow 4. At this time, the full cleaning procedure has been completed and the carriage 93 is again shifted sideways by further rotating the shaft 73. As a result and as shown in FIG. 15a, the sliding part 94b is forced against the stop 85b. Thereby the annular shell 79 is forced upward again and in the process the two levers are pivoted outward. The circle has been closed and the motion sequence can resume.

Lastly, FIG. 16 schematically shows the full rotational sequence of the shaft 73, i.e., of the two sections 75 and 77. Section 77 engages the aperture 80b and forces it into to-and-fro motion, whereas section 75 engages the aperture 80a and drives it into vertical reciprocation. The four snapshots of motion shown in FIGS. 15a through 15d are denoted by numerals 1 through 4 in FIG. 16. Various in-between rotational positions of the shaft 73 are shown schematically.

With respect to FIGS. 6 through 16, a special and illustratively preferred embodiment is shown and described herein, although the invention is in no way restricted thereto. As already explained in relation to FIGS. 1 through 4, it is obviously feasible to drive the tooth cleaning elements, such as bristles, in an arbitrary manner mechanically and/or electromagnetically. The significance of the invention is that the mechanical and/or electromagnetic drive is by means of the linkage between the main head and the cleaning head, that is, the actual drive motor can be mounted for instance in the grip, i.e., in the main head. The drive means can be cables, linkrod kinematics, shafts, gear systems, and the like or they can be electromagnetically driven components. Again, the design of the cleaning head is obviously arbitrarily modifiable, and the essential feature is that the cleaning elements mounted in the cleaning head, for instance cleaning bristles or clusters of bristles, shall be able to carry out at least two mutually separate motions at the teeth and in relation to them. Moreover, the cleaning head can be integral, for instance the described pan and the support can be integral.

It is claimed:

1. An automatic toothbrush comprising a main head attached to a grip; a cleaning head mounted on said main head in a manner which allows reciprocating movement of the cleaning head in relation to the main head; a support means mounted on said cleaning head and having cleaning elements mounted on the support means in such a manner that the cleaning elements will contact opposed sides of a tooth and adapt to reciprocating and rotational movement in relation to the main head; and a drive means which is operationally linked to the cleaning head and the support means to provide said reciprocating movement of the cleaning head and provide said reciprocating and rotational movement of the support means and cleaning elements and thus initiate and provide at least two sequences of motions to the cleaning elements in relation to a tooth.

2. Automatic toothbrush of claim 1 wherein said drive means is constructed and arranged in relation to the main head and the cleaning head mounted on the main head such that a linking element passes through a connection in said main head and said cleaning head to implement the movement of at least some of said cleaning elements.

3. Automatic toothbrush of claims 1 or 2 wherein the support means is concave as seen from a tooth.

4. Automatic toothbrush of claim 3 wherein the drive means implements at least said two sequences of motion in at least some of the cleaning elements, 5. Automatic toothbrush of claim 3 wherein the support means is U-shaped and comprises a base and a first lateral leg and a second lateral leg segment which are supported by and connected to the base so as to pivot relative toward or away from one another about a pin mounted approximate the base or at the end of each leg segment.

6. Automatic toothbrush of claim 5 wherein the drive means is operationally connected to the base to implement relative motion between the base and the main head or the cleaning head and to implement pivoting motions by the first leg segment and the second leg segment relative to the base.

7. Automatic toothbrush of claim 6 wherein the drive means provides each cyclic motion of the base and the first and second leg segments and the cleaning elements carry out closed two-dimensional motions in the plane of the support means and the path crosses the axis of symmetry of the support means in the direction of the base and main head.

8. Automatic toothbrush of claim 7 wherein the first and second leg segments are pre-stressed toward the axis of symmetry of the plane of the support means whereby the motion of the cleaning elements at the first and second leg segments occur under cleaning pressure directed from a tooth root or gum to a tooth crown and back with at least reduced pressure on account of the drive means opposing the pre-stressing.

9. Automatic toothbrush of claim 8 wherein the support means is controlled cyclically while being phase-shifted relative to the first and second leg segments in such manner that during a motion of the support means essentially vertically from the main head, the first and second leg segments are in their farthest possible pivoted positions from each other and in that during the opposite motion of the support means toward the main head, the first and second leg segments converge toward one another.

10. Automatic toothbrush of claims 1, or 2 wherein the cleaning head is composed of two parts wherein a first part is displaceably connected to a second part.

11. Automatic toothbrush according to claim 10 wherein said first part of the cleaning head includes a U-shaped frame having a base, a first leg and a second leg with inward pointing cleaning elements present on at least said first leg and said second leg which serve to clean a tooth.

12. Automatic toothbrush of claim 11 wherein the support means rests substantially jointly with the second part in a movable manner on the main head and the support means is mounted to be displaceable relative to the first part.

13. Automatic toothbrush of claim 11 wherein the first and second leg segments are pre-stressed by a leaf-spring means engaging the cleaning elements from opposite sides toward the plane of symmetry of the support means, the leaf spring means being mounted in such a manner to the base of the support means that the pivot point of the base shifts in the direction of the first and second leg segments when these leg segments are pivoted back in order that the spring force is different on account of different leverages and thereby the compression by the cleaning elements on the tooth remains approximately constant.

14. Automatic toothbrush of claims 1, or 2 wherein the drive means in the form of a shaft comprises in the connection area of the main head and the cleaning head, at least two excentric sections which implement at least one sequence of motions of at least some of the cleaning elements.

15. Automatic toothbrush of claim 14 wherein the shaft is driven in a substantially uniform rotation and one of the excentric sections is operationally linked to the support means to carry out the reciprocating motion relative to the main head and the other excentric section is operationally linked to the first and second leg segments to implement the pivoting motions relative to the base of the support means, the shaft sections being angularly offset from each other in such a way that the two sequences of motions are carried out at least by some of the cleaning elements in a phase-shifted manner.

16. Automatic toothbrush of claim 15 wherein the substantially linearly rotating shaft is mounted in a base unit supported so as to be transversely displaceable relative to the shaft, one of the excentric sections of the shaft implementing a first to-and-fro motion of the base unit transversely to the shaft axis in the direction from or toward the main head, said base unit being linked to the support means, a carriage element being mounted in the base unit and together with the base unit performs the first to-and-fro motion transversely to the shaft while furthermore also being supported so as to be displaceable transversely to the first direction of motion and transversely to the shaft axis in the base unit, the other excentric shaft section driving the carriage element into a second to-and-fro motion inside the base unit, said carriage element being linked for motion with an annular shell displaceably enclosing the base unit parallel to the first direction of motion in such a manner that when the carriage element is displaced in a direction toward the support means, the annular shell engages projections of the first and second leg segments and displace the cleaning elements away from the plane of symmetry of the support means plane, whereas when the carriage element is displaced in the opposite direction, the annular shell is moved away from the support means, whereby the first and second leg segments together with the cleaning elements are made to converge toward the plane of symmetry of the support.

17. Automatic toothbrush of claim 16 wherein the first and the second to-and-fro motions are mutually phase-shifted and directed at each other so that upon displacement of the base unit and the support means in the direction away from the main head, the annular shell is present near the support means to drive the first and second leg segments and the cleaning elements away from the plane of symmetry of the support means and particular tooth to be cleaned, and in that upon displacement of the base unit or the support means toward the main head the annular shell is away from the support means in order that the first and second leg segments shall converge toward the plane of symmetry in order to carry out a cleaning procedure from tooth root to tooth crown.

18. Automatic toothbrush of claim 2 wherein at least one camshaft serves as the drive means.

19. Automatic toothbrush of claim 2 wherein the cleaning elements are clusters of bristles.

* * * * *